United States Patent [19]
Kuusisto et al.

[11] Patent Number: 5,948,730
[45] Date of Patent: Sep. 7, 1999

[54] BIOCIDAL COMPOSITIONS COMPRISING MIXTURES OF HALOPROYNYL COMPOUNDS AND SULFUR CONTAINING TRIAZINES

[75] Inventors: Eeva-Liisa Kuusisto, Livingston; Kurt Hansen, W. Orange, both of N.J.

[73] Assignee: Troy Chemical Corporation, Newark, N.J.

[21] Appl. No.: 08/991,565

[22] Filed: Dec. 16, 1997

Related U.S. Application Data

[62] Division of application No. 08/436,554, May 8, 1995, Pat. No. 5,707,929.

[51] Int. Cl.⁶ .......................... A01N 43/34; A01N 43/66; A01N 47/10
[52] U.S. Cl. .......................... 504/155; 504/157; 514/245; 514/478; 514/479
[58] Field of Search .................. 504/155, 157; 514/245, 478, 479

[56] References Cited

U.S. PATENT DOCUMENTS

| | | | |
|---|---|---|---|
| 3,923,870 | 12/1975 | Singer | 260/482 C |
| 3,957,481 | 5/1976 | Bollinger et al. | 71/93 |
| 4,082,538 | 4/1978 | McRae | 71/125 |
| 4,259,350 | 3/1981 | Morisawa et al. | 424/308 |
| 4,592,773 | 6/1986 | Tanaka et al. | 71/88 |
| 4,616,004 | 10/1986 | Edwards | 514/63 |
| 4,640,705 | 2/1987 | Gabe et al. | 71/93 |
| 4,710,220 | 12/1987 | Pischky | 71/67 |
| 4,719,227 | 1/1988 | Schade et al. | 514/452 |
| 4,721,523 | 1/1988 | Schwamborn et al. | 71/93 |
| 4,915,909 | 4/1990 | Song | 424/28 |
| 4,945,109 | 7/1990 | Rayudu | 514/478 |
| 5,082,722 | 1/1992 | Guglielmo, Sr. | 428/255 |
| 5,190,580 | 3/1993 | Gruening | 106/18.32 |
| 5,209,930 | 5/1993 | Bowers-Daines et al. | 424/401 |
| 5,219,875 | 6/1993 | Sherba et al. | 514/373 |
| 5,328,926 | 7/1994 | Oppong | 514/372 |
| 5,374,631 | 12/1994 | Oppong et al. | 514/241 |
| 5,389,300 | 2/1995 | Schmitt et al. | 252/380 |

FOREIGN PATENT DOCUMENTS

| | | |
|---|---|---|
| 187 291 | 7/1984 | European Pat. Off. |
| 484 172 | 5/1992 | European Pat. Off. |
| 741 971 | 11/1996 | European Pat. Off. |
| 2438970 | 6/1980 | France |
| 4-134001 | 5/1992 | Japan |
| 2126092 | 3/1984 | United Kingdom |
| 2138292 | 10/1984 | United Kingdom |

*Primary Examiner*—Allen J. Robinson
*Attorney, Agent, or Firm*—Banner & Witcoff, Ltd.

[57] ABSTRACT

This invention is directed to a broad spectrum fungicide/algaecide composition which comprises a mixture of (a) at least one halopropynyl compound and (b) at least one sulfur-containing s-triazine, said mixture provided in an amount to prevent and/or protect a substrate from attack by one or more fungal and/or algael organisms. The composition can be used broadly in industrial systems and more particularly with substrates such as paints, coatings, stucco, concrete, stone, cementaceous surfaces, wood, caulking, sealants, textiles, and the like.

9 Claims, No Drawings

BIOCIDAL COMPOSITIONS COMPRISING MIXTURES OF HALOPROYNYL COMPOUNDS AND SULFUR CONTAINING TRIAZINES

This application is a divisional of application Ser. No. 08/436,554, filed May 8, 1995, now U.S. Pat. No. 5,707,929.

FIELD OF THE INVENTION

This invention is directed to a biocidal composition and particularly a synergistic mixture or combination of a halopropynyl compound and a sulfur-containing s-triazine.

BACKGROUND OF THE INVENTION

Both exterior and interior surfaces and substrates of all types, when exposed to common environmental conditions, e.g. moisture, are prone to attack, discoloration and various kinds of destruction by fungal and algael organisms. As a result, there is a great need and requirement for an effective and economical means to protect for extended periods of time both exterior and interior surfaces and various type substrates from the deterioration and destruction caused by such microorganisms.

Materials which need protection with a suitable antimicrobial composition controlling both fungal and algael microorganisms and their adverse effects include paints, coatings, stucco, concrete, stone, cementaceous surfaces, wood, caulking, sealants, and textiles as well as materials and other substances which may be attacked by fungi and/or algae.

Commercial products designed for the simultaneous control of fungi and algae on such substrates are available, but such products suffer from a number of disadvantages and especially their inability to maintain sufficient activity after leaching by water.

In addition, such products currently available in the marketplace are generally supplied as normally water-insoluble powders, as pastes, or as flowable dispersions which are difficult to incorporate in a manner to insure maximum effectiveness. On the other hand, an effective composition in the form of a solution would be highly desirable having advantages for ease of handling and incorporation in end use products and to insure proper distribution of the biocide on or in the surfaces and substrates to be protected, thus maximizing microbiological performance.

Thus, a broad spectrum biocide composition highly effective against both fungi and algae, and which is essentially unaffected by leaching with water, in an environmentally, toxicologically suitable liquid media has many advantages and is desirable for a wide number of uses in industry.

With respect to compositions and/or mixtures, methods of manufacture and/or uses and applications of combinations of fungicides and algaecides, the prior art and references describing these combinations is limited.

There are a number of organic compounds and especially certain carbamates, such as the halopropynyl carbamates which are known primarily for their fungicidal activity. 3-iodo-2 propynyl butyl carbamate, hereinafter referred to as IPBC, is the best known and the most widely used of the known haloalkynyl carbamate fungicides. In addition to its fungicidal activity, IPBC also has been associated with algaecidal activity. In this regard, Great Britain Patent 2,138,292 and U.S. Pat. Nos. 4,915,909 and 5,082,722 contain such disclosures. IPBC is a highly active broad spectrum fungicide. Nevertheless, its spectrum of action is sometimes incomplete against the broad range of naturally occurring fungal species. For this reason, U.S. Pat. No. 5,389,300 describes using a phenol derivative, such as o-phenylphenol, with an iodopropargyl compound, such as IPBC, for protecting freshly sawn timber from such pests.

Certain s-triazines are known for their algaecidal activity. They have been found to be especially effective for use in agricultural applications. One such example of this algacide is $N^2$ tertbutyl-$N^4$-ethyl-6-methylthio-1,3,5-triazine-2,4 diyldiamine and a second such example is 2-methylthio-4-tert-butylamino-6-cyclopropylamino-s-triazine. U.S. Pat. No. 4,710,220 for example, describes formulations containing a polyethoxylated compound and certain s-triazines, with $N^2$-tert-butyl-$N^4$-ethyl-6-methylthio- 1,3,5-triazine-2, 4-diyldiamine, hereafter referred to as Terbutryn, as one example. Even so, Terbutryn is probably more widely known as a herbicide, and in particular, is widely disclosed for use as a herbicide in combination with a variety of other compounds. For example, in U.S. Pat. No. 3,957,481 it is used in combination with metobromuron for controlling weeds when cultivating leguminosae and solana; in U.S. Pat. No. 4,640,705 and Great Britain Patent 2,126,092 it is used in combination with trifluralin and ethylfluralin respectively, for preemergent control of weeds, particularly blackgrass, in cereal crops and in French Patent 2,438,970 it is used with neburon and nitrofen to control weeds in winter wheat. Nowhere, however, has it been suggested to combine Terbutryn with a halopropynyl compound and particularly a haloalkynyl carbamate fungicide for any purpose.

In this regard, while U.S. Pat. No. 4,721,523 describes a herbicidal combination of certain widely-known carbamate derivatives with a photosynthesis-inhibiting compound, including as one of nine possible compound classes certain triazine derivatives (identifying Terbutryn as one of a dozen examples), the disclosed carbamates do not include the haloalkynyl carbamates.

In a similar fashion, while U.S. Pat. No. 5,374,631 describes using a mixture of an iodopropargyl compound, including IPBC, with an s-triazine to control fungal and bacterial growth in metalworking fluids, the only triazine identified is hexahydro-1,3,5-tris(2-hydroxyethyl)-s-triazine.

Thus, the prior art has completely failed to appreciate any benefit from combining a halopropynyl compound and particularly a haloalkynyl carbamate with a sulfur-containing s-triazine.

BRIEF DESCRIPTION OF THE INVENTION

The present invention is based on the surprising synergistic effect that a combination of a halopropynyl compound, and particularly a halopropynyl carbamate fungicide, and a sulfur-containing s-triazine algaecide has on the increased efficacy of the resulting combined product, especially against fungi.

In accordance with a preferred embodiment of the invention, it has now been discovered that synergistic combinations containing in particular both the fungicide, 3-iodo-2-propynyl butyl carbamate (IPBC) and the herbicide, $N^2$-tertbutyl-$N^4$-ethyl-6-methylthio-1,3,5-triazine-2,4 diyldiamine (Terbutryn) gives a surprising and unexpected biocidal effect against mold and blue-stain fungi. This increased biocidal effect has especially been shown to occur when the product is used against the fungi *Aureobasidium pullulans* and *Alternaria alternata*. This discovery is of outstanding commercial importance because the increased effect has especially been demonstrated after the test samples have been exposed to leaching with water. Particularly surprising is the good effect against *Alternaria alternata,* which often is found to be very difficult to control on exposed surfaces such as paints, coatings, stucco, concrete stone, cementaceous surfaces, wood, caulking, sealants, textiles, and the like.

Relative proportions of the two components in compositions according to the present invention may be varied widely since the combination also provides excellent algaecidal properties. Depending on the degree of environmental pressure on the exposed area, it can be an advantage to select and adjust the proportions of the two components relevant to and depending upon which organism is more problematic to control and for which maximum protection is desired.

DETAILED DESCRIPTION OF THE INVENTION

The present invention is directed to a synergistic combination of a halopropynyl compound, particularly a halopropynyl carbamate such as IPBC, and a sulfur-containing s-triazine, particularly Terbutryn.

A halopropynyl compound for use in the present invention can be identified by the following structure:

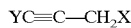

$YC{\equiv}C{-}CH_2X$ wherein Y is a halogen, preferably iodine and X can be (1) oxygen which is part of an organic functional group; (2) nitrogen which is an organic functional group; (3) sulfur which is part of an organic functional group; or (4) carbon which is part of an organic functional group.

The functional group of which oxygen is a part is preferably an ether, ester, or carbamate group. The functional group of which nitrogen is a part is preferably an amine, amide, or carbamate group. The functional group of which sulfur is a part is preferably a thiol, thiane, sulfone, or sulfoxide group. The organic functional group of which carbon is a part is preferably an ester, carbamate or alkyl group.

Examples of compounds which may be used as the halopropynyl compound fungicide of this invention are especially the fungicidally active iodopropargyl (iodopropynyl) derivatives. In this regard, please see U.S. Pat. Nos. 3,923,870, 4,259,350, 4,592,773, 4,616,004, 4,719,227, and 4,945,109, the disclosures of which are herein incorporated by reference. These iodopropynyl derivatives include compounds derived from propargyl or iodopropargyl alcohols such as the esters, ethers, acetals, carbamates and carbonates and the iodopropargyl derivatives of pyrimidines, tiazolinones, tetrazoles, triazinones, sulfamides, benzothiazoles, ammonium salts, carboxamides, hydroxamates, and ureas. Preferred among these compounds is the halopropynyl carbamate, 3-iodo-2-propynyl butyl carbamate. This compound is included within the broadly useful class of compounds having the generic formulas:

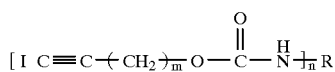

Wherein R is selected from the group consisting of hydrogen, substituted and unsubstituted alkyl, aryl, alkylaryl, and aralkyl groups having from 1 to 20 carbon atoms or from cycloalkyl and cycloalkenyl groups of 3 to 10 carbon atoms, and m and n are independently integers from 1 to 3, i.e., not necessarily the same.

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Especially preferred are such iodopropargyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

Examples of compounds which may be used as the sulfur-containing s-triazine component of this invention include the known, algaecidally active s-triazine compounds. Those included, without limitation thereto, are $N^2$-tert-butyl-$N^4$-ethyl-6-methylthio-1,3,5-triazine-2,4-diyldiamine and 2-methylthio-4-tert-butylamino-6-cyclopropylamino-s-triazine. These compounds are represented by the generic formula:

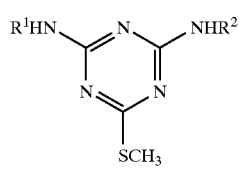

in which $R^1$, and $R^2$ independently of one another are each a $C_2$ to $C_6$ alkyl group or a $C_3$ to $C_6$ cycloalkyl.

As $C_2$–$C_6$-alkyl, $R^1$ and $R^2$ are for example: ethyl, propyl, isopropyl, butyl, secbutyl, pentyl, isopentyl, hexyl, 1,2-dimethylpropyl, 1,2-dimethylbutyl or 2,3-dimethylbutyl. Particularly preferred are branched-chain $C_3$–$C_6$-alkyl groups, for example isopropyl, 1,2-dimethylpropyl or tert-butyl.

As $C_3$–$C_6$-cycloalkyl, $R^1$ and $R^2$ are for example: cyclopropyl, cyclobutyl, cyclopentyl or cyclohexyl, cyclopropyl being preferred.

Preferred sulfur-containing s-triazines of the formula are those wherein $R^1$ is a branched-chain $C_3$–$C_6$-alkyl, for example isopropyl, 1,2-dimethylpropyl or tert-butyl; or wherein $R^1$ is cyclopropyl.

Likewise preferred are compounds of the formula wherein $R^1$ is ethyl or cyclopropyl, and wherein $R^2$ is tert-butyl, 1,2-dimethylpropyl or isopropyl.

Relative proportions of the halopropynyl compound and the sulfur-containing s-triazine in the composition can vary widely and an optimum proportion likely will be affected by the intended application and the particular compounds selected. In any event, it is expected that compositions containing a little as 1 part of the halopropynyl compound to 9 parts of the s-triazine and conversely as little as 1 part of the s-triazine to 9 parts of the halopropynyl compound will be useful. Typically, useful compositions will contain from 2:1 to 1:2 parts of the halopropynyl compound to the s-triazine and more usually from 2:1 to 1:1 relative parts by weight.

In accordance with the invention, the combined fungicidal and algaecidal constituents can be included in a final formulation for use in such end use applications as paints, coatings, stucco, concrete, stone, cementaceous surfaces, wood, caulking, sealants, textiles, and the like, in a broad range from about 0.004% to 2.0% active concentration. Such compositions can be prepared from highly concentrated compositions of the active ingredients by appropriate dilution. The optimum useful range is about 0.1% to 0.3% of combined products in the final formulations for such end use systems. With the use of such modified formulations in end use systems, it is possible to protect surfaces as well as other substrates for extended periods of time against growth from both algae and fungi.

Compositions of the present invention will generally be formulated by mixing the two active ingredients in a selected proportion with a liquid vehicle for dissolving or suspending the active components. The vehicle may contain a diluent, an emulsifier and a wetting-agent. Expected uses of the biocidal compositions include protection of wood, paint, coatings, adhesives, paper, textiles, plastics, cardboard, lubricants, caulkings, and the like. An extensive list of potential industries and applications for the present invention can be found in U.S. Pat. No. 5,209,930 which is herein incorporated by reference. The synergistic combinations of the halopropynyl compound fungicide, particularly a halo-propynyl carbamate, and the sulfur-containing s-triazine are preferably formulated as liquid mixtures, but may be provided as wettable powders, dispersions, or in any other suitable product type which is desirable and most useful, provided that the synergistic fungicidal and algaecidal activity are not affected. In this regard, the composition of the present invention can be provided as a ready-for-use product in the form of aqueous solutions and dispersions, oil solutions and dispersions, emulsions, aerosol preparations and the like or as a concentrate.

Useful solvents for the halopropynyl compound, particularly the preferred iodopropynyl butyl carbamate, and sulfur-containing s-triazine, especially Terbutryn, combination are several glycol ethers and esters like propylene glycol n-butyl ether, propylene glycol tert-butyl ether, 2(2-methoxymethylethoxy)-tripropyleneglycol methyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate and dibasic esters of several dicarboxylic acids and mixes thereof.

The preferred solvents for these products are propylene glycol n-butyl ether, 1-methoxy-2-propanol, and the dibasic isobutyl ester blend of succinic, glutaric and adipic acids.

When preparing formulations of the present invention for specific applications, the composition also will likely be provided with other adjuvants conventionally employed in compositions intended for such applications such as organic binding agents, additional fungicides, auxiliary solvents, processing additives, fixatives, plasticizers, UV-stabilizers or stability enhancers, water soluble or water insoluble dyes, color pigments, siccatives, corrosion inhibitors, antisettlement agents, anti-skinning agents and the like. Additional fungicides used in the composition are preferably soluble in the liquid vehicle.

According to the present invention, substrates are protected from infestation by fungal and algael organisms simply by treating said substrate with a composition of the present invention. Such treating may involve mixing the composition with the substrate, coating or otherwise contacting the substrate with the composition and the like.

A surprising aspect of the invention was found to be that the mixtures of a halopropynyl compound, and particularly a iodopropynyl carbamate and a sulfur-containing s-triazine are especially efficacious in controlling the mold and blue stain fungi *Aureobasidium pullulans* and *Alternaria alternata*. These two organisms are both generally present in air, soil and water, and appear on most surfaces when moisture is present. Accordingly, these two fungi are a major commercial problem on surfaces coated with paints and other wood protection products and on other treated surfaces since in a short time, they can create a very heavy, dark staining which not only discolors the surface but attacks the coating and destroys it as well. Thus, such pests have a very destructive overall effect and a method for their control has long been sought.

The fungi used in the tests, presented hereinafter, were selected because they are among the most problematic staining organisms which occur on exposed surfaces. While synergistic effects have been demonstrated against the specific organisms shown below in Tables 1 and 2, many other fungi can be controlled by these novel biocidal compositions.

The novel compositions of the invention contain, at least, one herbicide from the sulfur-containing s-triazine group which is not presently known to have any fungicidal effect. However, they are highly efficacious against algae growing on the same areas as the mold fungi. The halopropynyl compound, and particularly the iodopropynyl carbamate is a fungicide used for protection against staining organisms and wood destroying fungi. With the combination of these two biocides: a herbicide and fungicide it would be expected to obtain a product active against algae and fungi simultaneously. Surprisingly, it was found that the activity against the fungi *Aureobasidium pullulans* and *Alternaria alternata* was stronger than would be expected from any known data. The data obtained from a solution in which the two compounds have been combined clearly shows that a synergistic and unexpected effect between the two compounds occurs.

The following examples are presented to illustrate and explain the invention. Unless otherwise indicated, all references to parts and percentages are based on weight.

EXAMPLES

Example 1

The compositions of the invention were found to be effective against both algae and fungi. Specifically, algae and fungi which may be inhibited include without limitation, *Stichococcus basillaris, Chlorella vulgaris, Chlorella vulgaris* var. *viridis, Trentepohlia aurea, Aspergillus niger, Aureobasidium pullulans, Alternaria alternata*. The preferred combination of compounds, including an iodopropynyl carbamate and a sulfur-containing s-triazine were tested in various ratios from 2:1 to 1:6.

The biological tests were carried out separately for algae and for fungi. Detailed descriptions of the tests are outlined below.

In the algae test, an algae inoculum was prepared by washing a one-week old plate of each species into 100 ml isotonic water. The active formulations were applied on filter paper at the rate of 225 g/m$^2$. After a drying time of one week, the filter paper was divided into two parts, one part was immersed into tap water at room temperature, leached for 24 hours and then dried. The other part was allowed to remain unleached. 1.26 cm$^2$ discs were cut from the leached and unleached filter paper and placed on the agar plates. A suspension of 0.5 ml algae was spread over the plate and the test paper with an appropriate spatula.

The plates were incubated at 15° C. and evaluated after 2 weeks.

When the combination samples were tested against fungi, each sample was coated upon filter paper in duplicate, and then air dried for 1 week. One of the filter papers was exposed (leached) for 24 hours in room temperature tap water and air dried for 24 hours. Each sample was then cut into 1 inch squares of which 2 were placed in petri dishes containing solidified Malt Agar and seeded with *Aspergillus niger,* conidia and hypha fragments; 2 were placed in petri dishes containing solidified Malt Agar and seeded with *Aureobasidium pullulans,* conidia and hypha fragments, and 2 were placed in petri dishes containing solidified Malt Agar and seeded with *Alternaria alternata,* conidia and hypha fragments. The petri dishes were incubated for a period of 3 weeks at 28 degrees C.

Tables 1 and 2 show the results of the comparative tests which were carried out as described above. The formulations tested were comprised of 0.1% of 3-iodo-2-propynyl-butylcarbamate (IPBC), 0.1% and 0.2% of $N^2$ tertbutyl-$N^4$-ethyl-6-methylthio-1,3,5-triazine-2,4 diyldiamine (Terbutryn) and mixtures of 0.1% IPBC and 0.1% Terbutryn. Test results actually show that unexpected synergistic results in inhibition and growth reduction were obtained with the tested mixtures as compared with effects to be expected or predicted from the individual ingredients when tested against fungi, i.e., *Aspergillus niger, Aureobasidium pullulans* and *Alternaria alternata.*

TABLE 1

COMPARATIVE TEST RESULTS AGAINST ALGAE AND FUNGI OF IPBC, TERBUTRYN, AND THE COMBINATION OF IPBC AND TERBUTRYN

| | | ALGAE* | | A. NIGER | | A. PULLULANS | | A. ALTERNATA | |
|---|---|---|---|---|---|---|---|---|---|
| | % | Unleached | Leached | Unleached | Leached | Unleached | Leached | Unleached | Leached |
| IPBC | 0.1 | 4 | 4 | Z10 | Z8 | Z5 | 0 | Z2 | 0 |
| TERBUTRYN | 0.2 | Z25 | Z23 | 5 | 5 | 5 | 5 | 5 | 5 |
| IPBC + TERBUTRYN RATIO 1:1 | 0.2 | Z25 | Z23 | Z12 | Z8 | Z7 | Z4 | Z4 | Z2 |

Legend:
Z = Zone of Inhibition (in mm)
0 = No growth
1 = Trace Growth
2 = Light Growth
3 = Moderate Growth
4 = Heavy Growth
5 = Very Heavy Growth
*Test Algae Mixture: *Stichococcus basillaris, Chlorella Vulgaris, Chlorella Vulgaris* var. *viridis* and *Trentepohlia aurea*

TABLE 2

COMPARATIVE TEST RESULTS AGAINST ALGAE AND FUNGI OF IPBC, TERBUTRYN, AND THE COMBINATION OF IPBC AND TERBUTRYN

| | | ALGAE* | | A. NIGER | | A. PULLULANS | | A. ALTERNATA | |
|---|---|---|---|---|---|---|---|---|---|
| | % | Unleached | Leached | Unleached | Leached | Unleached | Leached | Unleached | Leached |
| IPBC | 0.1 | 4 | 4 | Z10 | Z8 | Z5 | 0 | Z2 | 0 |
| TERBUTRYN | 0.1 | Z25 | Z20 | 1 | 5 | 5 | 1 | 5 | 5 |
| IPBC + TERBUTRYN RATIO 1:1 | 0.2 | Z25 | Z23 | Z12 | Z8 | Z7 | Z4 | Z4 | Z2 |

Legend:
Z = Zone of Inhibition (in mm)
0 = No growth
1 = Trace Growth
2 = Light Growth
3 = Moderate Growth
4 = Heavy Growth
5 = Very Heavy Growth
*Test Algae Mixture: *Stichococcus basillaris, Chlorella Vulgaris, Chlorella Vulgaris* var. *viridis* and *Trentepohlia aurea*

Example 2

LIQUID FORMULATIONS—SYNERGISTIC COMBINATIONS

TABLE 3

| Ingredient | % W/W |
|---|---|
| A. 1:1 combination | |
| 3-iodo-2-propynyl butyl carbamate | 20 |
| $N^2$-terbutyl-$N^4$-ethyl-6-methylthio-1,3,5-triazine-2,4-diyldiamine | 20 |
| DBE dibasic ester | 3 |
| propylene glycol n-butyl ether | 57 |
| B. 1:1 combination | |
| 3-iodo-2-propynyl butyl carbamate | 20 |
| $N^2$-terbutyl-$N^4$-ethyl-6-methylthio-1,3,5-triazine-2,4-diyldiamine | 20 |
| Propylene glycol n-butyl ether | 60 |
| C. 2:1 combination | |
| 3-iodo-2-propynyl butyl carbamate | 26.6 |
| $N^2$-terbutyl-$N^4$-ethyl-6-methylthio-1,3,5-triazine-2,4-diyldiamine | 13.4 |
| Propylene glycol n-butyl ether | 60 |
| D. 1:2 combination | |
| 3-iodo-2-propynyl butyl carbamate | 13.4 |
| $N^2$-terbutyl-$N^4$-ethyl-6-methylthio-1,3,5-triazine-2,4-diyldiamine | 26.6 |
| Propylene glycol n-butyl ether | 60 |

A suitable reaction vessel equipped with an appropriate mixing unit is charged with the indicated amounts of solvents in Examples 2A through 2D of Table 3. The mixing unit is started and the indicated amounts of the carbamate and triazine compounds were added. Mixing was continued until the biocides were completely dissolved. The mixture was then filtered (with filter-aid) before transfer to appropriate containers.

A number of liquid formulations were prepared as described above and were then incorporated into paints by mixing. The precise composition of biocides are set forth in detail in Table 3. They were tested according to the method as described in Example 1. The test results showed synergistic activity against algae and fungi when the combinations of two ingredients of carbamate and triazine were used at 0.1 total active level. Shown in Table 3 are examples of the preferred solvents used in the preparation of liquid formulations.

TABLE 4

WETTABLE POWDER

| | Parts/Wt. |
|---|---|
| Example 3A - Ingredient | |
| 3-iodo-2-propynyl butyl carbamate (IPBC) | 520 |
| Silicon dioxide (silica) | 50 |
| Aluminum-Silicate (Clay) | 363 |
| Sulphonated Napthalene Condensate (Dispersant) | 60 |
| Alkylated Napthalene Sulphonate (Dispersant) | 7 |
| TOTAL | 1000 |
| Example 3B - Ingredients | |
| $N^2$-terbutyl-$N^4$-ethyl-6-methylthio-1,3,5-triazine-2,4-diyldiamine (Terbutryn) | 520 |
| Silicon dioxide (silica) | 50 |
| Aluminum-Silicate (clay) | 363 |

TABLE 4-continued

WETTABLE POWDER

| | Parts/Wt. |
|---|---|
| Sulphonated Napthalene Condensate (Dispersant) | 60 |
| Alkylated Napthalene Sulphonate (Dispersant) | 7 |
| TOTAL | 1000 |

A mixture was prepared as reported as Example 3A and Example 3B in ratio 1:1, using a shaker such as that used for similar paint products to produce a final product with 50% (w/w) activity.

The biocide formulation was incorporated into a styrene-acrylic paint formulation and tested according to the method described in Example 1 with similar synergistic results obtained.

TABLE 5

DISPERSION

| Ingredient A | Part/Wt. | Ingredient B | Part/Wt. |
|---|---|---|---|
| Propylene glycol | 7 | Propylene glycol | 7 |
| 3-iodo-2-propynyl butyl carbamate (IPBC) | 42 | $N^2$-terbutyl-$N^4$-ethyl-6-methylthio-1,3,5-triazine-2,4-diytdiamine (Terbutryn) | 42 |
| Aerosil (Hydrophobic Silica) | 1 | Aerosil (Hydrophobic Silica) | 1 |
| Mix | | | |
| Dispersant (Nonylethoxylate) | 2.0 | | 2.0 |
| Wetting Agent (Ethoxylated Sulphate) | 1.0 | Wetting Agent (Ethoxylated Sulphate) | 1.0 |
| Wetting Agent (Ethoxylated Sulphate) | 1.0 | Wetting Agent (Ethoxylated Sulphate) | 1.0 |
| Water | 34.40 | Water | 34.40 |
| Thickener | 1.0 | Thickener | 1.0 |
| | 1.00 | | 100 |

Ingredients A and B as shown in Table 5 were made using a dispersing mill (with cooling mantle) and using 1 mm glass beads to a fineness grind 5 microns or less. Some of the water may be omitted in order to obtain a thicker grinding paste as desired.

A mixture of A and B was made by combining the ingredients in a ratio of 1:1 to produce a synergistic combination product of the algaecide and the fungicide.

This product was then mixed into a styrene-acrylic paint using a laboratory mixer for a 5 minute mixing period. It was tested as described in Example 1 with similar results.

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

We claim:

1. A biocidal composition comprising a mixture of a halopropynyl compound and a sulfur-containing s-triazine in a proportion that exhibits synergistic biocidal activity, wherein said halopropynyl compound is 3-iodo-2-propynylbutyl carbamate and wherein said sulfur-containing s-triazine is $N^2$-tert-butyl-$N^4$-ethyl-6-methylthio-1,3,5-triazine-2,4-diyldiamine and wherein the halopropynyl compound and the sulfur-containing s-triazine are each present in a synergistic effective amount of from about 1 part halopropynyl compound to 9 parts s-triazine to about 9 parts halopropynyl compound to 1 part s-triazine.

2. The composition of claim 1 containing from about 0.004% to 2.0% of the mixture of said halopropynyl compound and said s-triazine.

3. The biocidal composition of claim 1 wherein said synergistic amount comprises from about 1 part halopropynyl compound to 2 parts s-triazine to about 2 parts halopropynyl compound to 1 part s-triazine.

4. A method of preparing the composition of claim 1 comprising mixing said halopropynyl compound and said sulfur-containing s-triazine in a liquid vehicle.

5. A method for protecting a substrate from fungal or algael infestation comprising treating said substrate with an effective amount of the composition of claim 1.

6. A biocidal composition comprising a solution of a halopropynyl compound and a sulfur-containing s-triazine in a suitable solvent, wherein said halopropynyl compound is 3-iodo-2-propynylbutyl carbamate and wherein said sulfur-containing s-triazine is $N^2$-tert-butyl-$N^4$-ethyl-6-methylthio-1,3,5-triazine-2,4-diyldiamine and wherein the halopropynyl compound and the sulfur-containing s-triazine are each present in a synergistic effective amount of from about 1 part halopropynyl compound to 9 parts s-triazine to about 9 parts halopropynyl compound to 1 part s-triazine.

7. The biocidal composition of claim 6 wherein said synergistic amount comprises from about 1 part halopropynyl compound to 2 parts s-triazine to about 2 parts halopropynyl compound to 1 part s-triazine.

8. A method of preparing the composition of claim 6 comprising dissolving said halopropynyl compound and said sulfur-containing s-triazine in a solvent.

9. A method for protecting a substrate from fungal or algael infestation comprising treating said substrate with an effective amount of the composition of claim 6.

* * * * *